United States Patent
Chatelain et al.

(10) Patent No.: US 6,623,703 B1
(45) Date of Patent: *Sep. 23, 2003

(54) PROCESS FOR PREPARING POLYNUCLEOTIDES ON A SOLID SUPPORT AND APPARATUS PERMITTING ITS IMPLEMENTATION

(75) Inventors: François Chatelain, Paris (FR); Viktor Kumarev, Villemonble (FR)

(73) Assignee: Proligo, LLC, Boulder, CO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/119,653

(22) Filed: Jul. 21, 1998

Related U.S. Application Data

(62) Division of application No. 08/358,556, filed on Dec. 14, 1994, now Pat. No. 5,869,643.

(30) Foreign Application Priority Data

Dec. 16, 1993 (FR) .............................. 93 15164

(51) Int. Cl.[7] .................................. C12M 1/00
(52) U.S. Cl. ....................... 422/131; 422/132
(58) Field of Search ................ 422/131, 132, 422/62; 210/198.2; 536/25.31, 25.34, 25.3; 566/25.34

(56) References Cited

U.S. PATENT DOCUMENTS

| | | | | |
|---|---|---|---|---|
| 4,192,798 A | * | 3/1980 | Verlander et al. | 530/334 |
| 4,353,989 A | | 10/1982 | Bender | 435/287 |
| 4,362,699 A | * | 12/1982 | Verlander et al. | 422/131 |
| 4,373,071 A | * | 2/1983 | Itakura | 525/375 |
| 4,458,066 A | * | 7/1984 | Caruthers et al. | 536/25.34 |
| 4,500,707 A | * | 2/1985 | Coruthers et al. | 536/25.34 |
| 4,517,338 A | * | 5/1985 | Urdea et al. | 536/25.3 |
| 4,689,405 A | * | 8/1987 | Frank et al. | 536/25.3 |
| 4,698,208 A | * | 10/1987 | Patchornik et al. | 422/62 |
| 4,746,490 A | * | 5/1988 | Saneii | 422/62 |
| 5,047,524 A | * | 9/1991 | Andrus et al. | 536/25.31 |
| 5,223,435 A | * | 6/1993 | Kohr | 436/89 |
| 5,241,998 A | * | 9/1993 | Ashraf-Khorassani | 141/67 |
| 5,252,296 A | * | 10/1993 | Zuckermann et al. | 422/116 |
| 5,262,530 A | * | 11/1993 | Andrus et al. | 536/25.31 |
| 5,298,259 A | * | 3/1994 | Lloyd et al. | 424/486 |
| 5,869,643 A | | 2/1999 | Chatelain et al. | 536/25.3 |

FOREIGN PATENT DOCUMENTS

| | | |
|---|---|---|
| EP | 0 114 599 | 1/1984 |
| EP | 0 130 739 | 6/1984 |
| EP | 70 181 491 | 10/1985 |
| EP | 0375278 A3 | 12/1989 |
| EP | 0541340 A2 | 11/1992 |
| WO | 82/03079 | 9/1982 |
| WO | WO 85/01224 | 9/1984 |
| WO | WO 91/17823 | 4/1991 |
| WO | WO 92/02535 | 7/1991 |
| WO | WO 95/01987 | * 1/1995 |

OTHER PUBLICATIONS

Karger, Snyder and Horvath, An introduction to Separation Science, John Wiley & Sons, 1973, pp. 124 and 288, 1973.*

* cited by examiner

*Primary Examiner*—Hien Tran
(74) *Attorney, Agent, or Firm*—Swanson & Bratschun, LLC

(57) ABSTRACT

The present invention relates to an apparatus for preparing polynucleotides on a solid support in a reactor comprising a column containing an immobilized solid support that is functionalized for polynucleotide synthesis. The solid support can be porous, and can be functionalized with a nucleoside or with a universal synthesis of polynucleotides.

11 Claims, 2 Drawing Sheets

DIAGRAM OF THE LARGESCALE SYNTHESIZER

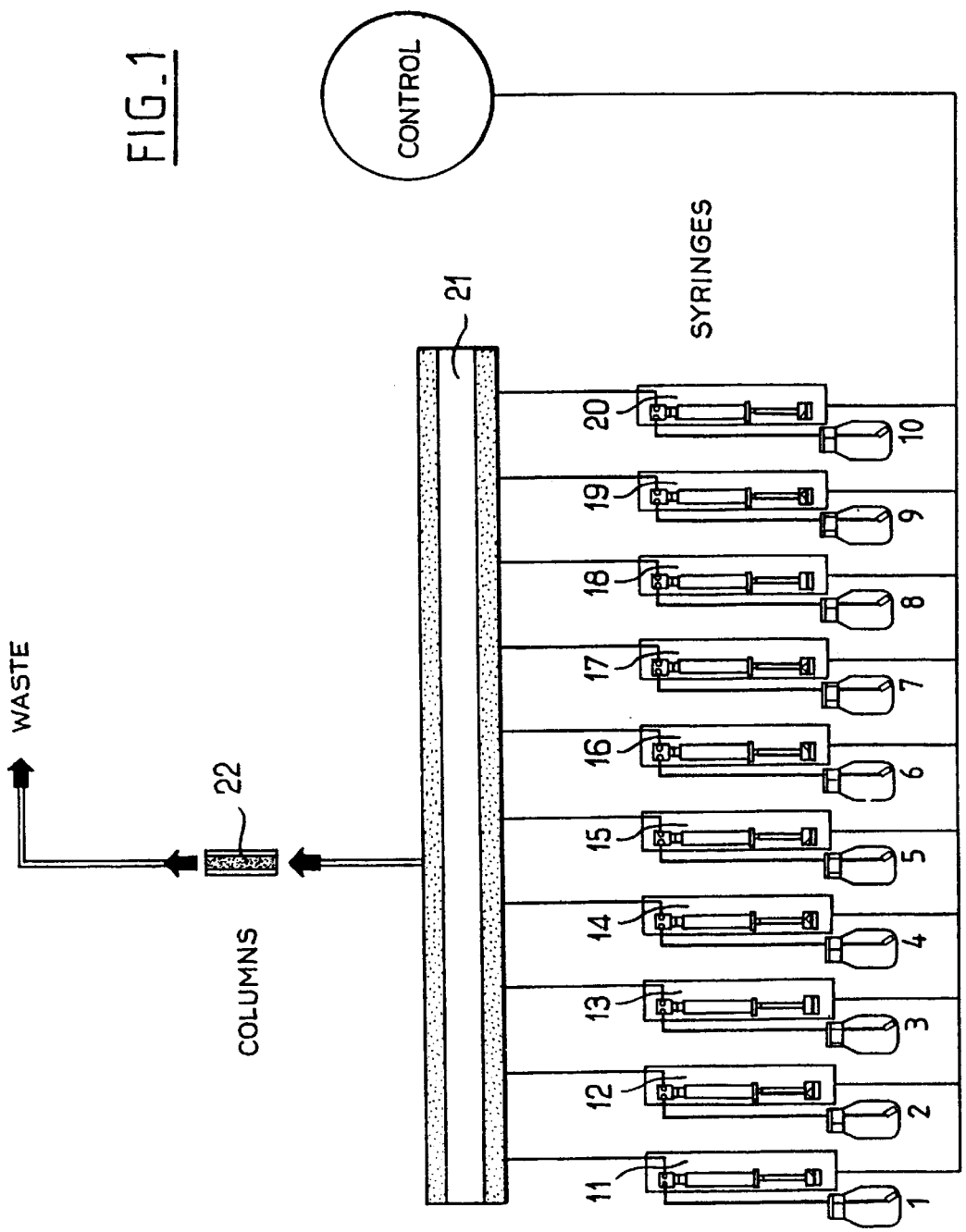

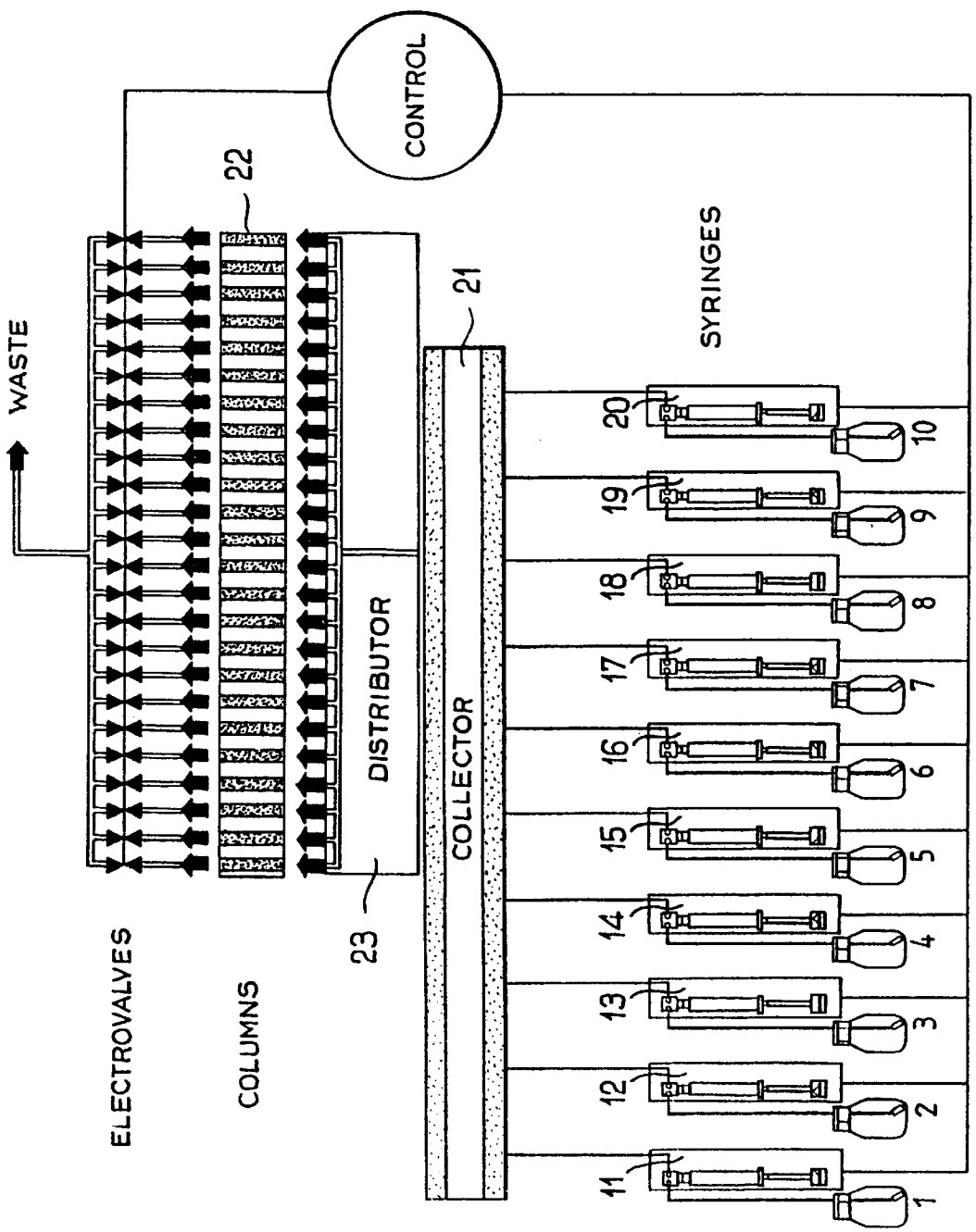
FIG._2

US 6,623,703 B1

PROCESS FOR PREPARING POLYNUCLEOTIDES ON A SOLID SUPPORT AND APPARATUS PERMITTING ITS IMPLEMENTATION

This application is a divisional of application Ser. No. 08/358,556, filed Dec. 14, 1994, now U.S. Pat. No. 5,869,643.

FIELD OF THE INVENTION

The present invention relates to a process for preparing polynucleotides on a solid support. The present invention also relates to a reactor containing a solid support and to a device including this reactor, which are useful in the process for preparing polynucleotides according to the invention.

BACKGROUND OF THE INVENTION

The synthesis of polynucleotides on a solid support is particularly used in automated syntheses of DNA or RNA oligonucleotides. In the present application, "polynucleotides" is understood to mean deoxyribonucleic acid or ribonucleic acid fragments or, more generally, polynucleotides or oligonucleotides where the bases, inter-nucleotide phosphate linkages, or alternatively the ribose rings of the bases, can be chemically modified in a known manner. This may be especially oligonucleotides with α or β anomers, oligonucleotides with inter-nucleotide linkage of the phosphorothioate or methyl phosphonate type, or alternatively oligothionucleotides.

The principle for the chemical synthesis of nucleic acids on a solid support is nowadays widely described in the specialist literature, and a number of apparatus are available on the market which perform automatically all or part of the synthesis steps. Among the chemical routes described, only the so-called phosphoramidites method (Caruthers et al.: EP 0,035,719 B1) is up until now sufficiently efficient to envisage the production of nucleic acids on an industrial scale.

The preparation of oligonucleotides or polynucleotides is carried out in a reactor containing a solid support and comprises the treatment of the solid support such as an inorganic polymeric support by a series of successive steps, each of the series leading to the addition of a new nucleotide on the support. The series of successive steps, or synthesis cycles, are carried out as many times as is required by the manufacture of an oligonucleotide or a polynucleotide of desired length.

In a process for synthesizing polynucleotides on a solid support, the solid support traditionally consists of glass beads of controlled porosity (CPG) or, more generally, of particles of a functionalized inorganic or organic polymer.

The techniques conventionally used involve the use of eight different reagents as solid supports, consisting of the said functionalized inorganic or organic polymer linked to a nucleoside A, T, C, G or U, depending on whether the sequence to be prepared contains, as first deoxyribo- or ribonucleotide A, T, C, G or U. Manufacturers therefore supply reactors in which one of these nucleosides has previously been attached to the support. Depending on whether the sequence starts with A, T, C, G or U, the appropriate reactor is then chosen. The elongation of this first nucleoside then occurs in the 3'→5', or 5'→3' direction, using coupling reagents.

Numerous supports have already been described in the literature for the solid phase synthesis of oligonucleotides. There may be mentioned organic polymers such as polystyrene (Nucleic A. Res. 1980, volume 8), polyacrylamide acryloylmorpholide, polydimethylacrylamide polymerized on kieselguhr (Nucleic Ac. Res. 9(7) 1691 (1980)).

Other supports described are of inorganic nature, in particular based on silica functionalized by a hydrocarbon radical carrying an NH2 and/or COOH group (J. Am. Chem., 105, 661 (1983)), or the support based on silica functionalized by a 3-aminopropyltriethoxysilane group whose use in phosphite and phosphoramidite synthesis for the preparation of oligonucleotides was described for the first time in European Patent No. 0,035,719.

There is known, from French Patent Application FR 93 08 498 and PCT/FR94/00842, a process for the solid phase synthesis of oligonucleotides in which a so-called "universal" support is used, that is to say a solid support which can be used regardless of the first nucleotide of the RNA or DNA to be synthesized, regardless of the type of monomeric reagent used during the synthesis, that is to say regardless of the type of substitution on the phosphate group in 3' or in 5', depending on whether the synthesis is carried out in the 5'→3' or 3'→5' direction.

In particular, the "universal nature" of the solid phase supports can be obtained by functionalization of the inorganic or organic polymer with a hydrocarbon radical containing glycol type groups in which an OH group and a nucleophilic group are present in the vicinal position, that is to say on two adjacent carbons, at the end of the hydrocarbon radical, it being possible for these two carbons to be optionally substituted by inert groups. "Inert group" is understood here to mean a group which does not react under the conditions encountered during the various steps of the synthesis on a solid support of nucleic acids according to the invention.

In a specific embodiment, a process for synthesizing polynucleotides comprises the following steps of:

1) condensing the OH group in 5' or 3' of the first nucleotide or of an oligonucleotide linked at its other 3' or 5' end to the said solid support, by means of a coupling agent, with the phosphate group optionally substituted respectively in position 3' or 5' of a monomeric nucleotide reagent protected in 3' and 5';

2) oxidizing or sulfurizing the phosphite type internucleotide linkage obtained in step 1) into a phosphate linkage respectively;

3) deprotecting the 5'-O or 3'-O end of the product obtained in step 2);

4) repeating steps 1) to 3) as many times as there are nucleotides to be added in order to synthesize the nucleic acid.

The above steps lead to an oligonucleotides linked to the solid support. The process comprises a final step of detaching the nucleic acid from the support and removing the groups for protecting the bases and, where appropriate, the 2'-O positions of the nucleic acid.

In the techniques where the solid support is already linked to a first nucleoside corresponding to the first nucleotide of the sequence to be prepared, before the start of the synthesis cycles, the said support generally contains a protection in 5' or 3' of the said nucleoside. In this case, the synthesis cycle starts with a deprotection step in acidic medium, in general a detritylation.

According to the variants used most commonly, the said monomeric nucleotide reagent corresponds to the formula:

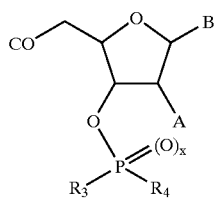

in which:

A represents H or an optionally protected hydroxyl group, is a purine or pyrimidine base whose exocyclic amine functional group is optionally protected, C is a conventional protective group for the 5'-OH functional group, x=0 or 1 with
  a) when x=1:
    $R_3$ represents H and $R_4$ represents a negatively charged oxygen atom, or
    $R_3$ is an oxygen atom and $R_4$ represents either an oxygen atom or an oxygen atom carrying a protecting group, and
  b) when x=0, $R_3$ is an oxygen atom carrying a protecting group and $R_4$ is either a hydrogen or a disubstituted amine group, when x is equal to 1, $R_3$ is an oxygen atom and $R_4$ is an oxygen atom, the method is in this case the so-called phosphodiester method; when $R_4$ is an oxygen atom carrying a protecting group, the method is in this case the so-called phosphotriester method, when x is equal to 1, $R_3$ is a hydrogen atom and $R_4$ is a hydrogen atom and $R_4$ is a negatively charged oxygen atom, the method is in this case the so-called H-phosphonate method, and when x is equal to 0, $R_3$ is an oxygen atom carrying a protecting group and $R_4$ is either a halogen, the method is in this case the so-called phosphite method and, when $R_4$ is a leaving group of the disubstituted amine type, the method is in this case the so-called phosphoramidite method.

The steps of a cycle of synthesis by the phosphoramidite method are conventionally the following:

1) condensation of the 5' terminal hydroxyl of a nucleoside or of an oligonucleotide covalently attached to the solid support with a phosphite type compound according to the reaction:

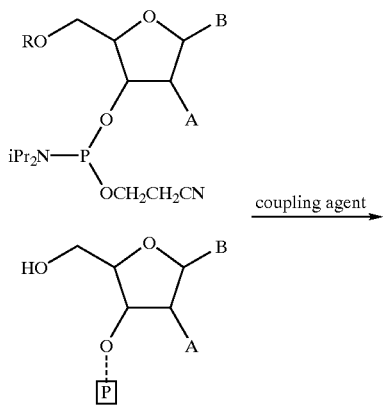

2) oxidation of the phosphite bond obtained to a phosphate according to the reaction:

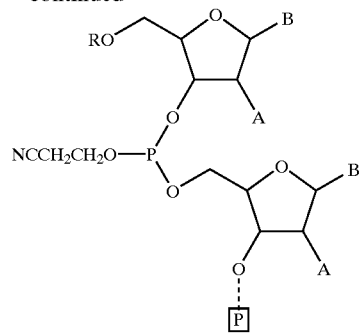

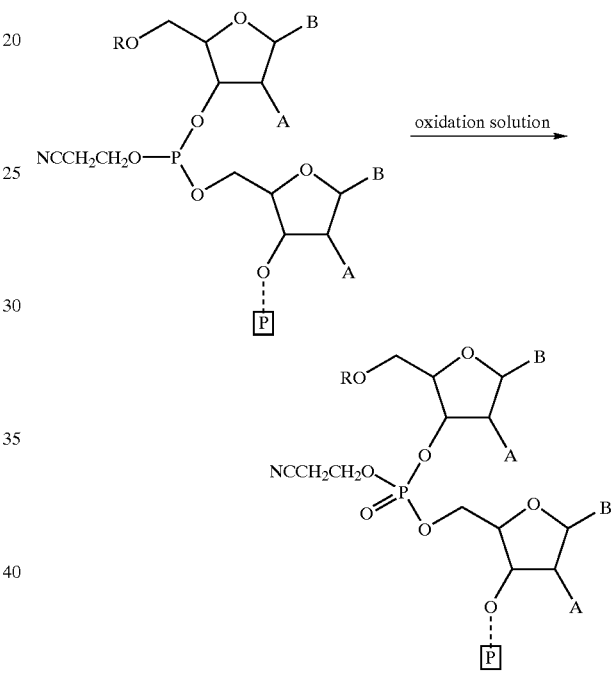

3) blocking of the hydroxyl groups of the unreacted nucleosides;

4) liberation of the 5' terminal hydroxyl from the last nucleoside so as to generate an active site for the next synthesis cycle.

Each nucleotide is sequentially added to the support by repeating steps 1 to 4. At the end of the synthesis, the oligonucleotide is separated from the support and freed of its protecting groups by a controlled hydrolysis reaction.

Commercial synthesizers specialized in the synthesis of oligonucleotides are designed so as to automatically carry out the synthesis steps described above. These synthesizers are generally composed of a reactor containing the solid support, a reagent mixer, one or several unit(s) for selecting the reagents and the vessels containing the said reagents. The synthesis steps are carried out by successively adding the selected reagents to the reactor. Most often, the solid support is washed with acetonitrile after each step.

The solid support is not immobilized and does not occupy the whole volume of the reactor but, in general, only half of the volume of the reactor, and in any case no more than three quarters, so as to allow adequate stirring of the solid phase.

The reactor, as used in commercial synthesizers, has the shape of a vessel crossed by the flow of reagents which causes the stirring (or fluidization) of the solid support. It is indeed considered that the stirring of the solid phase is essential because it allows better penetration of the solvents and reagents into the pores of the solid phase generally consisting of porous beads or porous membranes (see Methods in Molecular Biology: Protocols for Oligonucleotides and Analogs—Synthesis and Properties—Edited by Sudhir Agrawal—1993—Humana Press; Totowa, N.J., pages 442–444 and 454).

The mixer is situated upstream of the reactor, connected to it by a pipeline. The units for selecting the reagents generally consist of electrovalves and allow selective opening of the inlets/outlets of the hydraulic circuit as well as the routes for the passage of the reagents. The cohesion of the hydraulic system is ensured by a series of suitably connected tubes or capillaries. It is recommended to install the equipment in an air-conditioned room at 20° C., the temperature at which the reactions are performed.

While the efficiency of the reactions is sufficient under these conditions, the duration of the reactions and the required excess of reagents in order to carry out good washing by successive dilutions are the principal disadvantages of the synthesizers as described above. In this case, the consumptions of reagents and the duration of the syntheses are substantially greater than the values calculated on the basis of known laws of organic synthesis. These disadvantages were attributed to the limiting factor which the rate of diffusion of the reagents in the pores constitutes.

SUMMARY OF THE INVENTION

The aim of the invention is the improvement of the efficiencies of existing methods of synthesis of oligonucleotides.

The method according to the present invention consists in a modification of organic synthesis apparatuses and parameters so as to improve the productivity thereof. The improvements affect in particular the duration and the consumption of reagents necessary for carrying out a synthesis.

The subject of the present invention is also a reactor for preparing polynucleotides according to a process of the invention, the reactor being in the form of a column containing a solid support through which the solutions of reagents and/or solvents are circulated, wherein the solid phase constituting the solid support is immobilized in said reactor such that said solutions migrate in the column and through said solid phase according to a frontal progression, the successive solutions of each step of a synthesis cycle not mixing at all or very little.

In particular, the subject of the present invention is therefore a reactor which is useful in a process for preparing polynucleotides on a solid support, which consists of a cylindrical column completely filled with particles of porous materials constituting a solid support as described above.

The subject of the present invention is finally a device for the synthesis of polynucleotides on a solid support containing a thermostatted reactor and a thermostatted collector which performs the collection, the heating to the temperature of the reactor, then the mixing of the reagents before their introduction into the reactor.

Other advantages and characteristics of the present invention will appear in the light of the detailed description below.

BRIEF DESCRIPTION OF THE DRAWINGS

FIG. 1 illustrates a "LargeScale Synthesizer" of the invention.

FIG. 2 illustrates a "Multicolumn Synthesizer" of the invention.

DETAILED DESCRIPTION OF THE INVENTION

It was discovered according to the present invention that it is mainly the geometry of the vessel-type reactor in which the free particles of the solid support are stirred according to the principle of "pseudoliquid" phase reaction which has numerous disadvantages.

It was also discovered that several other parameters are also called into question which considerably reduce the productivity of the synthesizers:

the reagents used for the oxidation step (iodine solution, tetrahydrofuran, lutidine and water) are degraded over time, and the resulting reduction in reactivity rapidly induces a reduction in the efficiency of the synthesis; and the absence of thermostatting of the reactor and of the reagents leads to the loss of reproducibility of the syntheses.

The hydraulic system itself often comprises unusable dead volumes. The time spent by the reagents in these dead volumes and in the mixing chamber, in particular during the activation of phosphoramidite by the coupling agent, limits the reactivity of the transient species formed.

Accordingly, the present invention relates to a set of modifications made to the system described above which has the effect of improving the productivity by reducing the consumption of reagents and the durations of synthesis.

The essential characteristic of the process according to the present invention relates to the immobilization of the solid phase or to the method of filling the reactor with the solid phase.

The subject of the present invention is indeed a process for preparing polynucleotides on a solid support in a reactor in the form of a column through which solutions of reagents and/or solvents are circulated, wherein the solid phase constituting said solid support is immobilized in said reactor, and said solutions migrate in the column and through the solid phase according to a frontal progression, such that the successive solutions from each step of a synthesis cycle do not mix.

The subject of the present invention is also a process for preparing polynucleotides on a solid support in a reactor in the form of a column through which the solutions of reagents and/or solvents are circulated, wherein the reactor is a column completely filled with particles of a porous material constituting said solid support.

In this embodiment where the solid support consists of free particles of a porous material filling a column, the particles are also immobilized. The immobilization indeed results from the fact that by "completely filled column" there is understood here that the degree of filling with particles and the density of distribution of the particles in the column are such that the particles are sufficiently packed such that they can no longer move when a liquid crosses the column.

It may be only a portion of the column which is completely filled provided that the particles of the solid support are maintained by appropriate means in said a portion of the column.

In an advantageous embodiment, the column will have a cylindrical shape.

It is thus proposed, for the first time, to use a "chromatography column" type reactor, that is to say a column consisting of a cylindrical tube completely filled with the solid phase.

This type of column, homogeneously filled with the solid support, offers several advantages: the various solutions which follow each other in the reactor do not mix, or very little, there is therefore no phenomenon of dilution of the solutions by the previous reagent and the washing following each step of the synthesis cycle is thereby greatly facilitated. According to the chromatography column principle, the successive solutions introduced at one end of the column migrate according to a frontal progression, such that a solution "pushes" the preceding one.

It was indeed observed that the solid phases conventionally used in solid phase oligonucleotides synthesis are such that the affinity and the physicochemical interactions of the various reagents and solvents used are negligible and do not interfere with their diffusion through the solid phase other than by the desired chemical reactions.

It should be mentioned that, of course, in the interface region between the solutions, slight mixing may occur locally between the solutions when the circulation rates of the solutions are high. However, this mixing, which is localized at the interface, is in no way comparable with what is observed in prior processes for which the washes were based on the principle of dilution by mixing successive solutions.

Contrary to the conventional model, these reactors therefore make it possible to substantially reduce the volumes of reagents required. The useful flow rates are adjusted as a function of the diffusion constants and the kinetics of the reactions called into play. The duration of the synthesis cycles is thereby considerably reduced. For each type of particle, depending on its porosity, the flow rate of the reagents through the column should not exceed a certain value above which the reagents no longer diffuse inside the pores. This is a well known phenomenon in chromatography.

In addition, within the reactor and regardless of its size, the conditions are locally always identical. The system can therefore be applied to all scales of synthesis.

In particular, there may be mentioned materials consisting of inorganic polymers, especially glass, silica, metal oxides, or of organic polymers, especially cellulose, or optionally substituted polystyrene.

Preferably, the polymer is an inorganic polymer prepared based on glass or silica, especially a silica gel.

The said particles may consist of microbeads or agglomerated microfibers.

Preferably, in the reactor according to the present invention, there may be used as particles of the solid support porous microbeads, thereby providing the largest functionalized surface area in terms of weight of nucleosides linked to the polymer per weight of polymers. The size of the beads may range from 5 $\mu$m to 500 $\mu$m, more generally from 40 $\mu$m to 70 $\mu$m. The pores may optionally pass right through the microbeads. The diameter of the pores may range between 200 Å and 10,000 Å. Two pore sizes may be used, with wide pores (about 10,000 Å) and smaller pores (300 Å). This type of pore of variable size favors the diffusion of the solutions through the solid phase.

The reactor according to the present invention makes it possible to best exploit known laws of diffusion and kinetics of bimolecular chemical reactions according to which the reagents in solution diffuse very rapidly into the pores of the solid support and the kinetics of condensation of the free nucleoside with the 5'OH end of the oligonucleotides attached to the support is practically instantaneous.

The regulation of the temperature of the reactor and the reagents is another essential characteristic of the present invention which, so far, does not exist in any synthesizer on the market.

The working temperature is one of the parameters which directly and simultaneously influence the kinetics of the chemical reactions called into play, but also the stability of the reagents and the viscosity of the solutions. Contrary to all the prejudice which claims that the synthesis of the oligonucleotides decreases the efficiency above 30° C., it is recommended according to the present invention to thermostat the reactor at an optimal temperature of 45° C. The regulation of the temperature of the system makes it possible to act on the kinetics of the chemical reactions called into play as well as on the viscosity of the solutions used.

Advantageously, the reagents, that is to say the coupling reagents such as tetrazole, and the monomeric reagents, on the one hand, and/or the various reagents of the oxidizing solution, on the other hand, are mixed immediately upstream of the reactor, or optionally, just upstream of a system of distribution of the reagents in a multicolumn system. The unusable dead volumes are thereby reduced.

In particular, the reagents are heated before introducing them into the reactor and, where appropriate, before mixing them.

Indeed, if the reagents are heated only after mixing them, a mutual inactivation and a loss of reactivity on the column are observed. More precisely, early mixing (too far from the reactor) of the reagents can lead to undesirable side reactions. In particular, the mixing of the tetrazole (weak acid) and the phosphoramidites can result in the detritylation of part of the monomers. The phosphoramidites can then react with each other. This type of reaction leads to the formation of homopolymers which may or may not react with the oligonucleotide attached to the support. The formation of oligonucleotides which are longer than desired can be observed in this case. Whatever the case, the synthesis yield is always thereby reduced. Of course, these phenomena are accentuated by heating. It is therefore advisable to heat the reagents before mixing them.

In the reactors used before the present invention, above 30° C., the reagents become rapidly degraded. But, by means of the reactor according to the present invention, which favors the kinetics of the reactions, it is possible to increase the temperature up to 90° C. (between 20 and 90° C.), preferably the temperature of the reactor is adjusted between 30 and 60° C., especially to 45° C.

Advantageously, the deprotection step in acidic medium is performed with TFA (trifluoroacetic acid) in dichloromethane. A 1% v/v solution of trifluoroacetic acid in extra dry dichloroethane is especially used during the step for liberation of the terminal 5' hydroxyl functional group (step 4) by replacing the standard solution (2% dichloroacetic acid in dichloromethane). This recommendation makes it possible in particular to get rid of the possible phenomena of boiling of dichloromethane when the working temperature exceeds 40° C.

The mixing of acetic acid and pyridine causes an increase in the temperatures from 40° to 60° C., which facilitates the maintenance of the temperature at said temperatures.

By virtue of the very high coupling yields (probably greater than 99%) of the process according to the invention, the step of blocking (or "capping") the unreacted 5'-OH functional groups (step 3) proves, in most cases, not to be very efficient, or even completely pointless and can therefore be omitted. Thus, no accumulation of synthetic fragments of size n−1 is observed as would be expected if no capping step is performed. Probably, when the efficiency of the reactions is optimal, the unreacted species are permanently inaccessible.

According to another characteristic of the present invention, the oxidation step is performed with iodine in acetic acid and pyridine. Thus, in place of the conventional oxidation solution, two reagents are used separately, one consisting for example of an iodine solution saturated with glacial acetic acid, the other being ultrapure pyridine. These reagents are advantageous in that, at the oxidation step (step 2 above), these two solutions can be mixed in stoichiometric quantities at the inlet of the reactor. The mixture thus formed is injected into the reactor and instantaneously and quantitatively ensures the oxidation of the newly formed internucleotide bond. Thus, advantage is taken of the stability of the two separate solutions by indefinitely guaranteeing the reproducibility of the oxidation step.

Two oligonucleotides or polynucleotide synthesizers, designed on the basis of the technical improvements described above, were produced. The performances and the productivity of these two apparatus are thereby substantially increased compared to apparatus on the market.

The first synthesizer was designed to synthesize quantities of oligonucleotides between 50 $\mu$mol and 1 mmol. These performances can therefore be compared to those of commercial synthesizers which are present on the market and are capable of working at equivalent synthesis scales. This apparatus is called "LargeScale Synthesizer". It is represented in FIG. 1.

The function of the second apparatus is to synthesize, in parallel, 24 different oligonucleotides or polynucleotides. The scale of each synthesis is between 0.05 and 1 $\mu$mol. So far, this apparatus has no equivalent. Its productivity can be compared to that of 6 synthesizers—4 columns on the market. It is called "Multicolumn Synthesizer". It is represented in FIG. 2.

These two apparatus comprise:
- the vessels [(1) to (10)] containing the reagents, each comprising a syringe type positive displacement pumping module [(11) to (20)];
- a thermostatted collector [(21)] whose attributes are the collection, the heating and the regulation of the temperature and the mixing of the moving reagents.

The "LargeScale Synthesizer" is equipped with a "filled column" type thermostatted reactor (22) whose dimensions are adjusted as a function of the desired synthesis scale.

The "Multicolumn Synthesizer" is equipped with 24 microcolumns [(22)] of the same type as the "Large-Scale Synthesizer" but whose dimensions make it possible to work at the scales 0.05 $\mu$mol, 0.1 $\mu$mol, 0.2 $\mu$mol and 1 $\mu$mol. Between the collector and the reactors is a distributor [(23)] responsible for equally distributing the reagents between the 24 columns.

Finally, a block composed of 24 electrovalves, individually controlled at each column, makes it possible to select, at each synthesis step, the reactors "in service".

The volumes, the flow rates and the waiting times are under the control of a computer. The program controls the correct sequence and the execution of the cycles in conformity with the sequences to be synthesized.

In order to guarantee local conditions which are always identical regardless of the number of reactors in service, the "Multicolumn Synthesizer" functions according to an interactive mode. Thus, the volumes and the flow rates of each of the reagents are adjusted, at each instant, to the number of syntheses in progress.

A—Course of a Synthesis with phosphoramidite in the LargeScale Synthesizer

The synthesis scale is chosen at the time the program is initiated.

Each synthesis starts with an initialization cycle which makes it possible to wash and thermostat the reactor to the working temperature.

The program comprises five synthesis cycles corresponding to each of the four bases and to the possible modified bases.

The synthesis cycles can be broken down into synthesis steps or procedures which follow one another in the following chronological order:

1) Detritylation: liberation of the hydroxyl in position 5' of the nucleoside or of the oligonucleotide covalently attached to the solid support,
2) First washing;
3) Addition of the base: condensation of the phosphoramidite type monomer with the free 5' terminal hydroxyl of the nucleoside or of the oligonucleotide attached to the solid support. Formation of internucleotide bond;
4) Second washing;
5) Oxidation of the previously formed phosphite type internucleotide bond into phosphate;
6) Third washing.

These cycles are repeated as many times as is required by the oligonucleotide synthesis or the synthesis of a polynucleotide of desired length.

B—Course of a Synthesis in the Multicolumn Synthesizer

The synthesis scale is chosen at the time the program is initiated.

Each synthesis starts with an initialization cycle which makes it possible to wash and thermostat the reactors to the working temperature.

There is only one synthesis cycle which is repeated as many times as is required by the manufacture of the 24 oligo- or polynucleotides.

The cycle can be broken down in the following manner:
a) selection of the columns to be detritylated.
  1) Detritylation: liberation of the hydroxyl in position 5' of the nucleoside or of the oligonucleotide covalently attached to the solid support.
  2) First washing:
b1) Selection of the columns which should receive the A base.
  3-1) Addition of the A base: condensation of the phosphoramidite type A monomer with the free 5' terminal hydroxyl nucleoside or of the oligonucleotide attached to the solid support. Formation of the internucleotide bond.
b2) Selection of the columns which should receive the G base.
  3-2) Addition of the G base: condensation of the phosphoramidite type G monomer with the free 5' terminal hydroxyl of the nucleoside or of the oligonucleotide attached to the solid support. Formation of the internucleotide bond.
b3) Selection of the columns which should receive the T base.
  3-3) Addition of the T base: condensation of the phosphoramidite type T monomer with the free 5' terminal hydroxyl of the nucleoside or of the oligonucleotide attached to the solid support. Formation of the internucleotide bond.
b-4) Selection of the columns which should receive the C base.
  3-4) Addition of the C base: condensation of the phosphoramidite type C monomer with the free 5' terminal hydroxyl of the nucleoside or of the oligonucleotide attached to the solid support. Formation of the internucleotide bond.

c) Selection of the oxidizing columns.

4) Second washing.

5) Oxidation of the previously formed phosphite type internucleotide bond into phosphate.

6) Third washing.

Description of the Steps Mentioned Above

Each step can be described with reference to the diagrams provided for the synthesizers (FIGS. 1 and 2).

1) Detritylation: reagent no. 10, preferably a 1% v/v solution of trifluoroacetic acid in extra dry dichloroethane, is pushed through the reactor by means of the syringe module no. 10.

The volume necessary is between 2 and 10 times the volume of the empty reactor.

The flow rate in the column is less than 500 cm/min. This flow rate unit in cm/min in fact represents the linear speed of the solutions inside the column and is therefore independent of the diameter of the column.

The volume flow rates should be adjusted as a function of the diameter of the reactor. In order to change the size of the reactor while locally preserving the synthesis conditions, it is sufficient to modify the volume flow rate while ensuring that the linear speed inside the reactor, given in cm/min, does not change.

The flow rates which are used are compatible with the diffusion constants in the pores, that is to say that the linear speed of the solutions inside a column is not greater than the speed of diffusion through the pores. In the opposite case, there would be a low efficiency of the reagents and of the washes resulting in a decrease in the synthesis yields.

The total reaction time is between 10 and 120 seconds.

2) First washing: the reagent no. 1, preferably extra dry acetonitrile, is pushed through the reactor by means of the syringe module no. 1.

The volume required is between 2 and 10 times the volume of the empty reactor.

The flow rate in the column is less than 500 cm/min.

3) Coupling: the reagents no. 3, or no. 4, or no. 5 or no. 6, or no. 7, and no. 2, respectively a 0.1 M solution of each monomer and a 0.45% solution of tetrazole in acetonitrile, are conjointly pushed through the reactor by means of the syringe modules no. 3, or no. 4, or no. 5, or no. 6, or no. 7, and no. 2 respectively.

The ratios of the volumes and the flow rates of the reagents no. 3, or no. 4, or no. 5, or no. 6, or no. 7, and no. 2 may be different from 1.

The total volume required is between 2 and 10 times the volume of the empty reactor.

The overall flow rate in the column is less than 500 cm/min.

The reaction time is less than 1 minute.

4) Second washing: the reagent no. 1, preferably extra dry acetonitrile, is pushed through the reactor by means of the syringe module no. 1.

The volume required is between 0.5 and 5 times the volume of the empty reactor.

The flow rate in the column is less than 500 cm/min.

5) Oxidation: the reagents no. 8 and no. 9, respectively a saturated solution of iodine in glacial acetic acid and ultrapure pyridine, are conjointly pushed through the reactor by means of the syringe modules no. 8 and no. 9 respectively.

The ratios of the volumes and flow rates of the reagents no. 8 and no. 9 are equal to 1.

The total volume required is between 1 and 5 times the volume of the empty reactor.

The overall flow rate in the column is less than 500 cm/min.

The reaction time is less than 30 seconds.

6) Third washing: the reagent no. 1, preferably extra dry acetonitrile, is pushed through the reactor by means of the syringe module no. 1.

The volume required is between 1 and 5 times the volume of the empty reactor.

The flow rate in the column is less than 500 cm/min.

The following exemplary embodiment sizes serve to illustrate the process according to the invention.

EXAMPLES

Example 1

Synthesis of an Oligonucleotide, at the 30 $\mu$mol Scale, with the Aid of the LargeScale Synthesizer The apparatus used is that previously described.

The reactor used is a cylindrical glass column, of diameter 10 mm and height 25 mm.

The working temperature is 45° C.

The synthesis cycles are detailed in Table 1.

An oligodeoxynucleotide, 18 bases long, whose sequence is: d(ACG TTC CTC CTG CGG GAA) is synthesized under these conditions.

The reactor is carefully filled with 0.66 g of CPG 500 Å (CPG INC., USA), "derivatized" by the first A nucleoside. The capacity of the support is 45 $\mu$mol/g (density of 3 ml/g).

The synthesis scale is 30 $\mu$mol.

After a step of washing with acetonitrile, the synthesis cycle as described in Table 1 is performed 17 times.

Under these conditions, the oligonucleotide, of the desired length, retains the transient dimethoxytrityl group at the 5' terminal position.

The oligonucleotide is separated from the CPG and liberated from the permanent protecting groups by an appropriate treatment of the support, "derivatized" according to the method described above, with 10 ml of a 30% aqueous solution of ammonium hydroxide, for 16 hours at 55° C.

After adding 40 ml of absolute ethanol and 1 ml of a 3M aqueous solution of sodium acetate, the oligonucleotide is left to precipitate for two hours at 0C.

The precipitate is then filtered on a 1.2 pt lopridyne membrane (PALL S.A., FRANCE) and resolubilized in 10 ml of water.

After reading the optical density at 260 mm, 4000 O.D.U., that is to say 120 mg of crude synthesis mixture, are obtained.

The purity of the oligonucleotide of the desired length, estimated by HPLC on a reversed-phase column, is 88%.

Example 2

Synthesis of an Oligonucleotide, at the 77 $\mu$mol Scale, with the Aid of the LargeScale Synthesizer The apparatus used is the same as for the preceding example.

The reactor used is a cylindrical glass column, of diameter 10 mm and height 25 mm.

The working temperature is 45° C.

The synthesis cycles are detailed in Table 2.

An oligodeoxynucleotide, 18 base in length, whose sequence is: d(TTC CGC CAG GAG GAA CGT) was synthesized under these conditions.

The reactor is carefully filled with 0.66 g of High-Loaded CPG 500 Å, "derivatized" by the first T nucleoside. The capacity of the support is 110 μmol/g, its density 3 ml/g (MILLIPORE S.A., FRANCE).

The synthesis scale is 77 μmol.

After a step of washing with acetonitrile, we performed the synthesis cycle as described in Table 2 17 times.

Under these conditions, the oligonucleotide, of the desired length, retains the transient dimethoxytrityl group at the 5' terminal position.

The conditions for deprotection and recovery of the oligonucleotide are the same as those described in the preceding example.

After reading the optical density at 260 nm, 8,500 O.D.U., that is to say 255 mg of crude synthesis mixture, are obtained.

The purity of the oligonucleotides of the third length, estimated by HPLC on a reversed-phase column, is 84%.

Example 3

Synthesis of an Oligonucleotide, at the 100 μmol scale, with the Aid of the LargeScale Synthesizer The apparatus used is the same as for the previous example.

The reactor used is a cylindrical glass column, of diameter 15 mm and height 34 mm.

The working temperature is 45° C.

The synthesis cycles are detailed in Table 3.

An oligonucleotide, 56 bases in length, whose sequence is d(TAA CCA CAC TTT TTG TGT GGT TAA TGA TCT ACA GTT ATT TTT TAA CTG TAG ATC AT) is synthesized under these conditions.

The reactor is carefully filled with 2 g of CPG 500 Å, "derivatized" by the first T nucleoside. The capacity of the support is 50 μmol/g, its density 3 ml/g (MILLIPORE S.A., FRANCE).

The synthesis scale is 100 μmol.

After a step of washing with acetonitrile, we performed the synthesis cycle as is described in Table 3 55 times.

Under these conditions, the oligonucleotide, of the desired length, retains the transient dimethoxytrityl group at the 5' terminal position.

The conditions for deprotection and recovery of the oligonucleotide are the same as those described in the previous examples.

After reading the optical density at 260 nm, 31,000 O.D.U., that is to say 930 mg of crude synthesis mixture, are obtained.

The purity of the oligonucleotide of length 56 mers, estimated by HPLC on a reversed-phase column, is 61%.

Example 4

Simultaneous Syntheses of 24 Different Oligonucleotides with the Aid of the Multicolumn Synthesizer The reactors are metallic micro columns of diameter 1.5 mm and height 6 mm.

The working temperature is 50° C.

The synthesis cycles are detailed in Table 4.

We synthesized, under these conditions, the oligodeoxynucleotides whose sequences are given in Table 5.

The reactors are evenly filled with 2 mg of universal CPG 500 Å containing an epoxide group (prepared according to Example 1 of patent application FR 93 08 498). The capacity of the support is 50 μmol/g (GENSET S.A., FRANCE) (density: 3 ml/g).

The synthesis scale is 0.1 μmol.

After a step of washing with acetonitrile, we performed the operations described in Table 4 as many times as is required by the synthesis of the 24 oligodeoxynucleotides of Table 5.

The conditions for deprotection and recovery of the oligonucleotide are the same as those described in the preceding examples.

After reading the optical density at 260 nm, 11 O.D.U. are obtained on average from each of the oligonucleotides, that is to say 0.33 mg. The purity of the oligonucleotides, estimated by HPLC, on a reversed-phase column for the 5' O-Trityl oligodeoxynucleotides, and on an anion exchange column for the 5'OH oligonucleotides, exceeds 84%.

Comparative Example 5

Table 6 below presents the characteristics of the syntheses carried out with fluidized bed reactors marketed by APPLIED BIOSYSTEMS and MILLIPORE as described in the literature.

The synthesizers used are the following:

APPLIED SYNTHESIZER, model 394:
    reactor in the form of a column:
        diameter 5 mm
        height 6 mm
        volume 0.1 ml
    Solid support: CPG 500 Å (CPG INC., USA)
        capacity: 30 μmol/g
        density: 3 ml/g
    For a synthesis at the 0.2 μmol scale:
        6.7 mg of CPG, that is to say a volume of 0.02 ml and a degree of filling of 20%.

MILLIPORE SYNTHESIZER, model 8800:
    Reactor in the form of a 225 ml vessel which can be used with 1 to 15 g of CPG.

For our examples:
    "STANDARD" method for 100 μmol
        solid support: CPG 500 Å (MILLIPORE S.A., FRANCE)
        capacity: 30 μmol/g
        density: 3 ml/g
    For 100 μmol: 3.33 g of CPG
        that is to say 10 ml of phase and a degree of filling of 4.5%.
    "IMPROVED" method for 100 μmol
        solid support: HIGH-LOADED CPG 500 Å (MILLIPORE S.A., FRANCE)
        capacity: 100 μmol/g
        density: 3 ml/g
    For 100 μmol: 1 g of CPG
        that is to say 3 ml of phase and a degree of filling of 1.3%.

In comparison with the results described in Examples 1 to 4, the decrease in the duration of synthesis and the quantities of reagents is considerable. For the synthesis of 100 gmol:
    with the process according to the invention (Example 3 and Table 3), 118 ml of reagents and solvents are used and the duration of synthesis is 3 minutes per synthesis cycle;
    with a MILLIPORE column, 500 ml of reagents and solvents are used, and the duration of synthesis is 20 minutes per cycle.

TABLE 1

| SOLVENTS OR REAGENTS | VESSEL NO. | VOLUME | IND. FLOW RATE | TOTAL FLOW RATE | TIME |
|---|---|---|---|---|---|
| Dichloroethane, TFA 1% v/v | 10 | 20 ml | 72 ml/min | | 17 sec |
| Waiting time | | | | | 20 sec |
| Acetonitrile | 1 | 8 ml | 72 ml/min | | 7 sec |
| 0.45 M Tetrazole in acetonitrile | 2 | 3 ml | 60 ml/min | | 3 sec |
| 0.45 Tetrazole in acetonitrile plus | 2 | 6 ml | 36 ml/min | 48 ml/min | 10 sec |
| 0.1 M monomer in acetonitrile | 3, 4, 5, 6 or 7 | 2 ml | 12 ml/min | | |
| Waiting time | | | | | 20 sec |
| 0.45 M Tetrazole in acetonitrile | 2 | 1 ml | 60 ml/min | | 1 sec |
| Acetonitrile | 1 | 2 ml | 60 ml/min | | 2 sec |
| Iodine sat. with Acetic Acid plus | 8 | 2.5 ml | 30 ml/min | 60 ml/min | 5 sec |
| Pyridine | 9 | 2.5 ml | 30 ml/min | | |
| Acetonitrile | 1 | 10 ml | 60 ml/min | | 10 sec |
| TOTAL | | 57 ml | | | 1 min 35 sec |

TABLE 2

| SOLVENTS OR REAGENTS | VESSEL NO. | VOLUME | IND. FLOW RATE | TOTAL FLOW RATE | TIME |
|---|---|---|---|---|---|
| Dichloroethane, TFA 1% v/v | 10 | 20 ml | 72 ml/min | | 17 sec |
| Waiting time | | | | | 30 sec |
| Acetonitrile | 1 | 8 ml | 72 ml/min | | 7 sec |
| 0.45 M Tetrazole in acetonitrile | 2 | 3 ml | 60 ml/min | | 3 sec |
| 0.45 Tetrazole in acetonitrile plus | 2 | 6 ml | 36 ml/min | 48.6 ml/min | 10 sec |
| 0.1 M monomer in acetonitrile | 3, 4, 5, 6 or 7 | 2.1 ml | 12.6 ml/min | | |
| Waiting time | | | | | 40 sec |
| 0.45 M Tetrazole in acetonitrile | 2 | 1 ml | 60 ml/min | | 1 sec |
| Acetonitrile | 1 | 2 ml | 60 ml/min | | 2 sec |
| Iodine sat. with Acetic Acid plus | 8 | 2.5 ml | 30 ml/min | 60 ml/min | 5 sec |
| Pyridine | 9 | 2.5 ml | 30 ml/min | | |
| Acetonitrile | 1 | 10 ml | 60 ml/min | | 10 sec |
| TOTAL | | 57.1 ml | | | 2 min 05 sec |

TABLE 3

| SOLVENTS OR REAGENTS | VESSEL NO. | VOLUME | IND. FLOW RATE | TOTAL FLOW RATE | TIME |
|---|---|---|---|---|---|
| Dichloroethane, TFA 1% v/v | 10 | 20 ml | 84 ml/min | | 30 sec |
| Waiting time | | | | | 30 sec |
| Acetonitrile | 1 | 14 ml | 72 ml/min | | 15 sec |
| 0.45 M Tetrazole in acetonitrile | 2 | 6 ml | 60 ml/min | | 6 sec |
| 0.45 Tetrazole in acetonitrile plus | 2 | 14 ml | 36 ml/min | 48 ml/min | 25 sec |
| 0.1 M monomer in acetonitrile | 3, 4, 5, 6 or 7 | 5 ml | 12 ml/min | | |
| Waiting time | | | | | 45 sec |
| 0.45 M Tetrazole in acetonitrile | 2 | 3 ml | 60 ml/min | | 3 sec |
| Acetonitrile | 1 | 6 ml | 60 ml/min | | 6 sec |
| Iodine sat. with Acetic Acid plus | 8 | 5 ml | 30 ml/min | 60 ml/min | 10 sec |
| Pyridine | 9 | 5 ml | 30 ml/min | | |
| Acetonitrile | 1 | 20 ml | 60 ml/min | | 15 sec |
| TOTAL | | 118 ml | | | 3 min 05 sec |

TABLE 4

| STEP | Dichloroethane 1% v/v TFA Detritylation | Acetonitrile Wash 1 | 0.45 M Tetrazole Coupling | 0.45 M Tetrazole 0.1 M Monomers Coupling | 0.45 M Tetrazole Wash 2 | Acetonitrile Wash 2 | Sol. of Iodine sat. Pyridine Oxidation | Acetonitrile Wash 3 | TOTAL VOLUME (ml) | TIME/CYCLE (min) |
|---|---|---|---|---|---|---|---|---|---|---|
| VESSEL NO. | 10 | 1 | 2 | 3, 4, 5, 6 or 7 | 2 | 1 | 8 and 9 | 1 and 2 | | |

TABLE 4-continued

| STEP | | Dichloroethane 1% v/v TFA Detritylation | Aceto-nitrile Wash 1 | 0.45 M Tetrazole Coupling | 0.45 M Tetrazole 0.1 M Monomers Coupling | 0.45 M Tetrazole Wash 2 | Aceto-nitrile Wash 2 | Sol. of Iodine sat. Pyridine Oxidation | Aceto-nitrile Wash 3 | TOTAL VOLUME (ml) | TIME/CYCLE (min) |
|---|---|---|---|---|---|---|---|---|---|---|---|
| 1 COLUMN | VOLUME (ml) | 0.8 | 0.4 | 0.0375 | 0.08 | 0.025 | 0.4 | 0.1 | 0.4 | 2.2425 | |
| | FLOW RATE (ml/min) | 6 | 4.8 | 2.25 | 2.94 | 1.5 | 4.8 | 3 | 4.8 | | 0.48 |
| 2 COLUMNS | VOLUME (ml) | 1.2 | 0.6 | 0.075 | 0.16 | 0.05 | 0.6 | 0.15 | 0.6 | 3.435 | |
| | FLOW RATE (ml/min) | 9 | 7.2 | 4.5 | 2.94 | 3 | 7.2 | 3.15 | 7.2 | | 0.52 |
| 3 COLUMNS | VOLUME (ml) | 1.6 | 0.8 | 0.1125 | 0.24 | 0.075 | 0.8 | 0.2 | 0.8 | 4.6275 | |
| | FLOW RATE (ml/min) | 12 | 9.6 | 6.75 | 5.88 | 4.5 | 9.6 | 3.3 | 9.6 | | 0.52 |
| 4 COLUMNS | VOLUME (ml) | 2 | 1 | 0.15 | 0.32 | 0.1 | 1 | 0.25 | 1 | 5.82 | |
| | FLOW RATE (ml/min) | 15 | 12 | 9 | 8.82 | 6 | 12 | 3.45 | 12 | | 0.53 |
| 5 COLUMNS | VOLUME (ml) | 2.4 | 1.2 | 0.1875 | 0.4 | 0.125 | 1.2 | 0.3 | 1.2 | 7.0125 | |
| | FLOW RATE (ml/min) | 18 | 14.4 | 11.25 | 11.76 | 7.5 | 14.4 | 3.6 | 14.4 | | 0.53 |
| 6 COLUMNS | VOLUME (ml) | 2.8 | 1.4 | 0.225 | 0.48 | 0.15 | 1.4 | 0.35 | 1.4 | 8.205 | |
| | FLOW RATE (ml/min) | 21 | 16.8 | 13.5 | 14.7 | 9 | 16.8 | 3.75 | 16.8 | | 0.54 |
| 7 COLUMNS | VOLUME (ml) | 3.2 | 1.6 | 0.2625 | 0.56 | 0.175 | 1.6 | 0.4 | 1.6 | 9.3975 | |
| | FLOW RATE (ml/min) | 24 | 19.2 | 15.75 | 17.64 | 10.5 | 19.2 | 3.9 | 19.2 | | 0.55 |
| 8 COLUMNS | VOLUME (ml) | 3.6 | 1.8 | 0.3 | 0.64 | 0.2 | 1.8 | 0.45 | 1.8 | 10.59 | |
| | FLOW RATE (ml/min) | 27 | 21.6 | 18 | 20.58 | 12 | 21.6 | 4.05 | 21.6 | | 0.56 |
| 9 COLUMNS | VOLUME (ml) | 4 | 2 | 0.3375 | 0.72 | 0.225 | 2 | 0.5 | 2 | 11.7825 | |
| | FLOW RATE (ml/min) | 30 | 24 | 20.25 | 23.52 | 13.5 | 24 | 4.2 | 24 | | 0.57 |
| 10 COLUMNS | VOLUME (ml) | 4.4 | 2.2 | 0.375 | 0.8 | 0.25 | 2.2 | 0.55 | 2.2 | 12.975 | |
| | FLOW RATE (ml/min) | 33 | 26.4 | 22.5 | 26.46 | 15 | 26.4 | 4.35 | 26.4 | | 0.57 |
| 11 COLUMNS | VOLUME (ml) | 4.8 | 2.4 | 0.4125 | 0.88 | 0.275 | 2.4 | 0.6 | 2.4 | 14.1675 | |
| | FLOW RATE (ml/min) | 36 | 28.8 | 24.75 | 29.4 | 16.5 | 28.8 | 4.5 | 28.8 | | 0.58 |
| 12 COLUMNS | VOLUME (ml) | 5.2 | 2.6 | 0.45 | 0.96 | 0.3 | 2.6 | 0.65 | 2.6 | 15.36 | |
| | FLOW RATE (ml/min) | 39 | 31.2 | 27 | 32.34 | 18 | 31.2 | 4.65 | 31.2 | | 0.59 |
| 13 COLUMNS | VOLUME (ml) | 5.6 | 2.8 | 0.4875 | 1.04 | 0.325 | 2.8 | 0.7 | 2.8 | 16.5525 | |
| | FLOW RATE (ml/min) | 42 | 33.6 | 29.25 | 35.28 | 19.5 | 33.6 | 4.8 | 33.6 | | 0.59 |
| 14 COLUMNS | VOLUME (ml) | 6 | 3 | 0.525 | 1.12 | 0.35 | 3 | 0.75 | 3 | 17.745 | |
| | FLOW RATE (ml/min) | 45 | 36 | 31.5 | 38.22 | 21 | 36 | 4.95 | 36 | | 0.60 |
| 15 COLUMNS | VOLUME (ml) | 6.4 | 3.2 | 0.5625 | 1.2 | 0.375 | 3.2 | 0.8 | 3.2 | 18.9375 | |
| | FLOW RATE (ml/min) | 48 | 38.4 | 33.75 | 41.16 | 22.5 | 38.4 | 5.1 | 38.4 | | 0.60 |
| 16 COLUMNS | VOLUME (ml) | 6.8 | 3.4 | 0.6 | 1.28 | 0.4 | 3.4 | 0.85 | 3.4 | 20.13 | |
| | FLOW RATE (ml/min) | 51 | 40.8 | 36 | 44.1 | 24 | 40.8 | 5.25 | 40.8 | | 0.61 |
| 17 COLUMNS | VOLUME (ml) | 7.2 | 3.6 | 0.6375 | 1.36 | 0.425 | 3.6 | 0.9 | 3.6 | 21.3225 | |
| | FLOW RATE (ml/min) | 54 | 43.2 | 38.25 | 47.04 | 25.5 | 43.2 | 5.4 | 43.2 | | 0.61 |
| 18 COLUMNS | VOLUME (ml) | 7.6 | 3.8 | 0.675 | 1.44 | 0.45 | 3.8 | 0.95 | 3.8 | 22.515 | |
| | FLOW RATE (ml/min) | 57 | 45.6 | 40.5 | 49.98 | 27 | 45.6 | 5.55 | 45.6 | | 0.62 |
| 19 COLUMNS | VOLUME (ml) | 8 | 4 | 0.7125 | 1.52 | 0.475 | 4 | 1 | 4 | 23.7075 | |
| | FLOW RATE (ml/min) | 60 | 48 | 42.75 | 52.92 | 28.5 | 48 | 5.7 | 48 | | 0.62 |
| 20 COLUMNS | VOLUME (ml) | 8.4 | 4.2 | 0.75 | 1.6 | 0.5 | 4.2 | 1.05 | 4.2 | 24.9 | |
| | FLOW RATE (ml/min) | 63 | 50.4 | 45 | 55.86 | 30 | 50.4 | 5.85 | 50.4 | | 0.62 |
| 21 COLUMNS | VOLUME (ml) | 8.8 | 4.4 | 0.7875 | 1.68 | 0.525 | 4.4 | 1.1 | 4.4 | 26.0925 | |
| | FLOW RATE (ml/min) | 66 | 52.8 | 47.25 | 58.8 | 31.5 | 52.8 | 6 | 52.8 | | 0.63 |
| 22 COLUMNS | VOLUME (ml) | 9.2 | 4.6 | 0.825 | 1.76 | 0.55 | 4.6 | 1.15 | 4.6 | 27.285 | |
| | FLOW RATE (ml/min) | 69 | 55.2 | 49.5 | 61.74 | 33 | 55.2 | 6.15 | 55.2 | | 0.63 |
| 23 COLUMNS | VOLUME (ml) | 9.6 | 4.8 | 0.8625 | 1.84 | 0.575 | 4.8 | 1.2 | 4.8 | 28.4775 | |
| | FLOW RATE (ml/min) | 72 | 57.6 | 51.75 | 64.68 | 34.5 | 57.6 | 6.3 | 57.6 | | 0.64 |
| 24 COLUMNS | VOLUME (ml) | 10 | 5 | 0.9 | 1.92 | 0.6 | 5 | 1.25 | 5 | 29.67 | |
| | FLOW RATE (ml/min) | 75 | 60 | 54 | 67.62 | 36 | 60 | 6.45 | 60 | | 0.64 |

TABLE 5

| COLUMN NO. | OLIGO | 5' Trityl | No bases | 5'-3' SEQUENCE |
|---|---|---|---|---|
| 0 | OLIGO1 | YES | 12 | TTT TTT TTT TTT |
| 1 | OLIGO2 | NO | 12 | TTT TTT TTT TTT |
| 2 | OLIGO3 | YES | 15 | TTT TTT TTT TTT TTT |
| 3 | OLIGO4 | NO | 15 | TTT TTT TTT TTT TTT |
| 4 | OLIGO5 | YES | 18 | TTT TTT TTT TTT TTT TTT |
| 5 | OLIGO6 | NO | 18 | TTT TTT TTT TTT TTT TTT |
| 6 | OLIGO7 | YES | 12 | AAA AAA AAA AAA |
| 7 | OLIGO8 | NO | 12 | AAA AAA AAA AAA |
| 8 | OLIGO9 | YES | 15 | AAA AAA AAA AAA AAA |
| 9 | OLIGO10 | NO | 15 | AAA AAA AAA AAA AAA |
| 10 | OLIGO11 | YES | 18 | AAA AAA AAA AAA AAA AAA |
| 11 | OLIGO12 | NO | 18 | AAA AAA AAA AAA AAA AAA |
| 12 | OLIGO13 | YES | 12 | CCC CCC CCC CCC |
| 13 | OLIGO14 | NO | 12 | CCC CCC CCC CCC |
| 14 | OLIGO15 | YES | 15 | CCC CCC CCC CCC CCC |
| 15 | OLIGO16 | NO | 15 | CCC CCC CCC CCC CCC |
| 16 | OLIGO17 | YES | 18 | CCC CCC CCC CCC CCC CCC |
| 17 | OLIGO18 | NO | 18 | CCC CCC CCC CCC CCC CCC |
| 18 | OLIGO19 | YES | 12 | AGT CAG TCA GTC |
| 19 | OLIGO20 | NO | 12 | AGT CAG TCA GTC |
| 20 | OLIGO21 | YES | 15 | AGT CAG TCA GTC AGT |
| 21 | OLIGO22 | NO | 15 | AGT CAG TCA GTC AGT |
| 22 | OLIGO23 | YES | 18 | AGT CAG TCA GTC AGT CAG |
| 23 | OLIGO24 | NO | 18 | AGT CAG TCA GTC AGT CAG |

TABLE 6

| SYNTHESIZERS | ABI 394 | MILLIPORE | MILLIPORE |
|---|---|---|---|
| CHARACTERISTICS | 4 COLUMNS | LARGE-SCALE | LARGE-SCALE |
| SYNTHESIS SCALE | 0.2 μmol | 100 μmol | 100 μmol |
| METHOD | STANDARD* | STANDARD** | IMPROVED** |
| REAGENTS | (ml) | (ml) | (ml) |
| MONOMERS 0.1 M | 0.110 | 5 | 2.62 |
| TETRAZOLE SOLUTION | 0.400 | 20.3 | 19 |
| CAP A (acetic anhydride) | 0.290 | 9 | 6.25 |
| CAP B (N-methylimidazole) | 0.260 | 11.6 | 8.65 |
| DEBLOCK (TCA/DCM) | 1.100 | 84.3 | 68.75 |
| IODINE SOLUTION | 0.350 | 40 | 33 |
| ACETONITRILE | 8.000 | 376 | 286.25 |
| TOTAL | 10,510 | 546.2 | 424.52 |
| TIME PER CYCLE | 6 min | 20 min | 22 min |

*APPLIED BIOSYSTEMS Instruction manual for the ABI 394 synthesizer
**N.D. SINHA, S. FRY; 3rd CAMBRIDGE SYMPOSIUM Oligonucleotides & Analogues, 5–8 Sept. 1992 POSTER COMMUNICATION

What is claimed is:

1. A synthesizer for preparing polynucleotides which comprises a thermostatted reactor comprising a column, through which solutions, reagents, and/or solvents can flow and which contains a solid support functionalized with reactive groups that form covalent bonds with nucleosides, wherein the solid support is packed and immobilized in said column, such that the solutions migrate in the column and throughout the solid phase according to a frontal progression, whereby successive solutions from each step of a synthesis cycle do not mix, and wherein the reactor is maintained at a temperature between 30° C. and 90° C.

2. The synthesizer of claim 1, wherein the column's solid support comprises particles of a porous material.

3. The synthesizer of claim 2, wherein the particles of porous material are porous microbeads.

4. The synthesizer of claim 1 further comprising a thermostatted collector which performs collection of reagents, heating of the reagents, and mixing of the reagents before their introduction into the reactor.

5. The synthesizer of claim 1 wherein the solid support is functionalized for the universal synthesis of polynucleotides.

6. The synthesizer of claim 5 wherein the solid support has been functionalized with a nucleotide reagent of the formula:

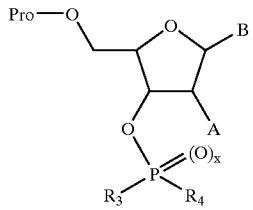

wherein A represents H or an optionally protected hydroxyl group; B represents a purine or pyrimidine base, the exocyclic amine of which is optionally protected; Pro represents a protecting group; x is 0 or 1, and each of $R_3$ and $R_4$ is independently H, an oxygen atom, an oxygen atom bound to a protecting group, or a disubstituted amine group, with the proviso that: if x is 1, $R_3$ is H and $R_4$ is a negatively charged oxygen atom, or $R_3$ is an oxygen atom and $R_4$ is an oxygen atom bound to a protecting group and $R_4$ is either H or a disubstituted amine group.

7. The synthesizer of claim 1 wherein the solid support is functionalized with a nucleoside.

8. The synthesizer according to claim 1, wherein said reactor has a thermostat setting between 30° C. and 60° C.

9. The synthesizer according to claim 1, wherein the reactor has a thermostat setting of about 45° C.

10. The device according to claim 4, wherein said reactor has a thermostat setting between 30° C. and 60° C.

11. The device according to claim 4, wherein the reactor has a thermostat setting of about 45° C.

* * * * *